United States Patent [19]

DeVincent

[11] Patent Number: 5,229,120

[45] Date of Patent: Jul. 20, 1993

[54] TREATMENT FOR COCAINE ABUSE

[76] Inventor: James F. DeVincent, 6032 105 Ave. North, Pinellas Park, Fla. 34666

[21] Appl. No.: 831,456

[22] Filed: Feb. 5, 1992

[51] Int. Cl.⁵ .......................... A61K 35/78; A61K 9/72
[52] U.S. Cl. .................................. 424/195.1; 424/40; 131/280; D27/100
[58] Field of Search ............... 424/195.1, 40; 131/280; D27/100

[56] References Cited

U.S. PATENT DOCUMENTS 5,089,502  2/1992  Sudilovsky ........................ 514/274
5,124,340  6/1992  Jaffe et al. ........................ 514/356

Primary Examiner—John W. Rollins
Attorney, Agent, or Firm—Richard C. Litman

[57] ABSTRACT

A composition and method for the treatment of drug abuse which comprises the administration by means of inhalation of an effective amount of a therapeutic smoke from a composition derived from a mixture of natural ingredients, primarily from grain products. The smoke from a composition consisting of whole ground rye, cornstarch, corn silk, and red clover can be breathed in from the surrounding atmosphere of an enclosed environment. A milder composition consisting of whole ground rye, cornstarch, corn silk, red clover, and wheat bran in unit form is particularly suitable for administration by smoking. The compositions produce a therapeutic smoke upon burning which when inhaled or smoked are effective for the treatment of cocaine habituation by blocking the reinforcing properties of the drug and for alleviating the unpleasant symptoms accompanying withdrawal from cocaine dependency.

9 Claims, No Drawings

TREATMENT FOR COCAINE ABUSE

This invention relates generally to a therapeutic composition and method for the treatment of drug abuse. More particularly, the present invention pertains to a method for suppressing cocaine habituation and a method of treatment during withdrawal from cocaine dependency by inhalation of the smoke of a therapeutic composition derived from an admixture of natural ingredients.

BACKGROUND OF THE INVENTION

Cocaine abuse is a major health problem in the United States and has reached epidemic proportions in recent years as more addictive forms of the drug have become available. In addition to the many sociological problems arising from cocaine abuse, there are adverse medical consequences from the use of this drug, such as acute intoxication marked by convulsions and cardiac arrhythmias. Chronic cocaine use is generally associated with increasing toxicity and behavioral pathology, and can result in the progressive development of seizures. Also, addiction to intravenous cocaine use is likely to increase the risk of AIDS, both through needle sharing and through the immuno-suppressive effects of the drug.

The mechanisms underlying the reinforcing effects of cocaine is not fully understood, particularly since this drug exhibits activities as both a potentiator and depressant of catecholaminergic systems. Thus, the initial effects of cocaine are known to enhance the activity of such neurotransmitters as dopamine, norepinephrine, epinephrine and serotonin, for example, which provides an immediate inducement to the use of the drug. Subsequent effects include depressing the biological characteristics of such neurotransmitters by blocking their uptake in the nervous system, which serves as an recurring inducement to undertake the repeatedly use of cocaine. This dual-action symptomology of cocaine is difficult to disrupt since the fundamental physiological and psychological processes responsible for the cocaine habituation syndrome remain largely unidentified. However, there is a strong consensus that dopaminergic neural systems play a critical role in cocaine reinforcement.

Although dopaminergic antagonists have shown some success in blocking the reinforcing effects of cocaine in experimental animals, there is at present no uniformly effective pharmacotherapy for cocaine dependence. Attempts to treat users of cocaine by administering a less harmful or less pleasurable drug in its place have yielded inconsistent results. Such treatment programs can result in a substitute addiction and may even stimulate relapse to cocaine abuse. In addition, abstinent treatment programs have met with limited success, largely because of the unpleasant symptoms accompanying cocaine withdrawal. These withdrawal symptoms include irritability, anxiety, depression, headaches and various other pains throughout the body. In many cases, the pain and discomfort become so severe upon cessation of cocaine dependency that abstinent persons abruptly return to the abused drug in an attempt to alleviate withdrawal symptoms.

There is therefore a substantial need to provide a non-addictive therapeutic treatment for cocaine abuse that is not only capable of interrupting the cocaine habituation syndrome, but also has the capability of alleviating the symptoms attendant upon withdrawal.

SUMMARY OF THE INVENTION

It is, accordingly, a primary object of the present invention to provide a composition and method for the treatment of drug abuse, particularly cocaine dependence.

It is a further object of the invention to provide such treatment so as to effect a discontinuation of such drug habituation and to alleviate the unpleasantness accompanying cocaine withdrawal.

It is a still further object of the invention to provide a non-addictive composition which may be conveniently administered by means of inhalation without a prescription.

These and other objects are accomplished in accordance with one embodiment of the present invention which provides a method for the treatment of cocaine abuse which comprises administering through inhalation an effective amount of a therapeutic smoke from a composition consisting of an admixture of whole ground rye (Secale cereale), cornstarch (Zea mays), corn silk (Zea mays) and red clover (Trifolium pratense). This composition is administered by inhaling the gaseous products resulting from burning the mixture of natural ingredients in a confined area. The therapeutic composition of the present embodiment acts quicker, lasts longer and is more readily absorbed by the body than corresponding prescription medicines administered orally.

In accordance with another embodiment of the invention, there is provided a therapeutic composition for treating drug abuse which is suitable for smoking comprising a mixture of whole ground rye (Secale cereale), cornstarch (Zea mays), wheat bran (Triticum satirum), corn silk (Zea mays) and red clover (Trifolium pratense). This particular mixture of grain products and herb may be fabricated into a narrow tube enclosed in cigarette paper or placed in a pipe for smoking.

The compositions of the present invention produce a therapeutic smoke upon burning which when inhaled has been found effective for the treatment of cocaine habituation by blocking the reinforcing properties of the drug and for easing the disturbing symptoms attendant upon cessation of cocaine intake.

The foregoing and other aspects, advantages and objects of the invention may be more fully appreciated by reference to the following detailed description.

DETAILED DESCRIPTION OF THE PREFERRED EMBODIMENTS

In accordance with a preferred embodiment of the present invention, the composition for treating cocaine abuse contains a mixture of naturally-derived ingredients, primarily from grain products, consisting of:
(a) about 30–50% by weight of whole ground rye,
(b) about 10–15% by weight of cornstarch,
(c) about 20–25% by weight of corn silk, and
(d) about 20–25% by weight of red clover.

The rye ingredient may be reduced to flakes or a coarse to fine powder by grinding, pulverizing and the like to produce a particulate material with substantially all the nutrient components of the whole grain remaining in the product. All of the grain products (a), (b) and (c) are commercially available and may be readily obtained without further processing. The red clover herb ingredient is also readily available and is primarily used in the present composition as a filler. This herb is preferably dried to facilitate burning of the therapeutic composition.

In the preparation of the composition of this particular embodiment, the four ingredients in their approximate weight percentages are thoroughly mixed together to form an intimate mixture. The mixture may then be placed in any suitable container, and thereafter burned by the application of a flame to produce a therapeutic smoke. Alternatively, the ingredients can be separately pulverized and combined with a sufficient amount of water to form a mixture of a moist granular consistency. The moist mixture is then shaped into any desired unit configuration and dried in an oven, for example, to remove substantially all of the moisture therefrom, such that subsequent burning of the shaped unit mixture is not effected.

The mode of administration contemplated by the present embodiment of the invention is through inhalation, by incorporating the therapeutic smoke from the ignited mixture of grain products and herb in an enclosed environment such as a room. The occupant(s) of the enclosed environment or person(s) undergoing drug treatment breaths in an effective amount of the smoke from the surrounding atmosphere of the room.

The term "effective amount" is intended herein to mean the total amount of smoke breathed in, retained and absorbed into the bloodstream to produce a therapeutically effective result. For purposes of the present embodiment, this amount may generally be from about 10 micrograms up to about 1000 micrograms, for example. The calculated amount is based on the assumption that the total amount of therapeutic substance effectively taken up by the body is about 10% of the breathed in and retained vaporous substance.

It should be understood that the frequency and duration of treatment may vary, depending on the level of cocaine intake prior to withdrawal, as well as the body weight and state of health of the person undergoing treatment. There is no upper limit as to the number of treatments per day which can be safely tolerated since there is no risk of the smoke from the mixture of naturally-derived ingredients being administered in an overdose. However, it is necessary that the person be relatively drug free during the treatment program of the present invention. Also, the treatment program should be administered regularly during the initial stages of withdrawal to effect the desired result.

Typically, a person undergoing treatment during the initial days of cocaine withdrawal is placed in a closed room containing from about 10 up to about 100 micrograms per liter in the air of smoke from the therapeutic composition of the invention. A composition having 11.2 g of whole ground rye, 2.8 g cornstarch, 7 g corn silk and 7 g of dried red clover, based on a 1 oz. total weight, has been found to be particularly effective. The subject person slowly breaths at an approximate rate of 10 liters per minute for a period of between about 10–30 minutes, at intervals of ½ to 2 hours, for example. Over a ten-day period the treatment was repeated. During treatment, the subject experienced no serious discomfort or pain due to withdrawal and subsequent to treatment it was confirmed that cocaine use had discontinued.

In accordance with another preferred embodiment of the present invention, a composition for treating cocaine abuse is provided which can be effectively administered by smoking a unit formulation containing a mixture consisting of:

(a) about 15–25% by weight of whole ground rye,
(b) about 5–10% by weight of cornstarch,
(c) about 20–30% by weight of corn silk,
(d) about 20–30% by weight of red clover, and
(e) about 15–25% by weight of wheat bran.

This substantially milder mixture of grain products and herb may be fabricated into a unit cigarette product or placed in a pipe for smoking. A composition consisting of about 20% by weight of whole ground rye, about 8% by weight of cornstarch, about 27% by weight of corn silk, 25% by weight of red clover, and about 25% by weight of wheat bran, wherein all weight percents are based on total ingredients, has been found to be particularly effective for purposes of the present embodiment.

In the preparation of the composition of this particular embodiment, the five ingredients in their approximate weight percentages are thoroughly mixed together. Preferably, the mixture is then divided into portions of about 1–1.5 grams, and each portion wrapped in appropriate paper and smoked as one would a regular cigarette. While the number of cigarettes containing the composition of the present invention may vary, in most cases about 5 to about 10 such cigarettes smoked at equally spaced intervals throughout the day will generally provide effective results. The present treatment may continue for as short a period as several weeks to as long as several months. The total time is difficult to predict on an individual basis because of the inestimable factors conducive to successful treatment, such as motivation, intelligence and dependability of the drug abuser. Detailed drug histories and other studies may be taken to determine a person's resistance to treatment.

Preliminary tests using the cigarette formulation of the present invention has been carried out on a number of confirmed cocaine addicts. There has been reported a 100% cure rate of addiction for at least three months after treatment with no adverse withdrawal symptoms. In a typical case, a 43 year old male subject using two or three grams of street grade cocaine a week administered nasally or by I.V. injection was treated in accordance with this particular embodiment of the invention. The treatment consisted of smoking an average of eight 1.55 g units in "cigarette" form of the mixture of grains and herb per day. Each unit cigarette consisted of 0.30 g of whole ground rye, 0.12 g of cornstarch, about 0.40 g of corn silk, 0.37 g of red clover, and 0.37 g of wheat bran. During treatment no serious pain was reported and after treatment which lasted for three weeks, the subject remained free of cocaine for six months.

Preliminary studies indicate that the compositions of the present invention modify the reinforcing properties of cocaine by assisting in the neural uptake of neurotransmitters, particularly dopamine and norepinephrine. This interpretation is consistent with the evidence that chronic cocaine use ultimately results in the depletion of neurotransmitters, giving rise to a feeling of depression, whereas the present treatment appear to be linked to neurotransmitters by an enhancing effect thereon, resulting in a customary sense of well being without an euphoric feeling. It is noteworthy that other therapeutic treatments for cocaine abuse do not attain such results as the present invention. For example, treatment with imipramine or desipramine does not block the concurrent use or "high" of cocaine and may even encourage its use by blocking the depression induced by cocaine. Also, bromocryptine, which otherwise appears suitable, is conductive to producing panic and hallucinations so that patients can not be relied upon to continue its administration.

Abusers of drugs other than cocaine that appear to be linked to neurotransmitters may likely benefit from treatment in accordance with the present invention. Potential benefactors of the present treatment include abusers of such neuotransmitter-linked drugs as amphetamines, phencyclidine (PCP) or certain "designer" drugs.

It should be understood that the suggested interpretation by which the present therapeutic compositions interrupt the cocaine abuse syndrome is merely proposed as a theoretical guide. It is not intended that the present invention be limited to any particular theory or mechanism involving interrelated biological systems.

It should be further understood that there may be various changes and modifications of the representative embodiments herein chosen for purposes of description without departing from the spirit and scope of the invention. Accordingly, the foregoing descriptions are not to be interpreted as restrictive of the invention beyond that necessitated by the following claims.

I claim:

1. A composition for treating cocaine abuse comprising an effective amount of a mixture consisting of:
    (a) about 30–50% by weight of whole ground rye,
    (b) about 10–15% by weight of cornstarch,
    (c) about 20–25% by weight of corn silk, and
    (d) about 20–25% by weight of red clover.

2. A composition for treating cocaine abuse comprising an effective amount of a mixture consisting of:
    (a) about 15–25% by weight of whole ground rye,
    (b) about 5–10% by weight of cornstarch,
    (c) about 20–30% by weight of corn silk,
    (d) about 20–30% by weight of red clover, and
    (e) about 15–25% by weight of wheat bran.

3. A method for treating cocaine abuse comprising administering to a cocaine abuser by inhalation an effective amount of a therapeutic smoke from the composition of claim 1.

4. The method according to claim 3 wherein the therapeutic smoke is incorporated within an enclosed environment.

5. The method according to claim 4 wherein the enclosed environment contains from about 10 up to about 100 micrograms per liter of air.

6. The method according to claim 3 wherein the amount of therapeutic smoke breathed in, retained and absorbed into the bloodstream of the cocaine abuser is from about 10 micrograms up to about 1000 micrograms.

7. A method for treating cocaine abuse comprising administering to a cocaine abuser by smoking a unit formulation containing the composition of claim 2.

8. The method according to claim 7 wherein said unit formulation comprises about 1–1.5 grams of the composition.

9. The method according to claim 8 wherein the formulation is fabricated into a cigarette product for smoking.

* * * * *